(12) United States Patent
Sai

(10) Patent No.: US 8,963,090 B2
(45) Date of Patent: Feb. 24, 2015

(54) TERAHERTZ-WAVE GENERATING APPARATUS AND MEASURING UNIT EQUIPPED WITH THE SAME

(75) Inventor: Hironobu Sai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/116,681

(22) PCT Filed: Apr. 23, 2012

(86) PCT No.: PCT/JP2012/061502
§ 371 (c)(1),
(2), (4) Date: Nov. 8, 2013

(87) PCT Pub. No.: WO2012/153666
PCT Pub. Date: Nov. 15, 2012

(65) Prior Publication Data
US 2014/0084163 A1    Mar. 27, 2014

(30) Foreign Application Priority Data
May 11, 2011    (JP) .................................. 2011-106229

(51) Int. Cl.
*G01J 5/02*    (2006.01)
*H01S 3/08*    (2006.01)
(Continued)

(52) U.S. Cl.
CPC ........ *H01S 3/08013* (2013.01); *G01N 21/3581* (2013.01); *G01N 21/55* (2013.01); *G01N 21/59* (2013.01); *H01S 3/10023* (2013.01); *G01N 2201/08* (2013.01)
USPC ..................................................... 250/341.1

(58) Field of Classification Search
CPC .. G02B 6/02328; G02B 6/10; G02F 2203/13; H01S 3/302; H01S 3/06754; G01N 21/3581

USPC ...................... 250/338.1–338.5, 341.1–341.8
See application file for complete search history.

(56) References Cited

U.S. PATENT DOCUMENTS 8,229,304 B1 * 7/2012 Pepper et al. .................. 398/214
8,681,421 B1 * 3/2014 Pepper et al. .................. 359/344
(Continued)

FOREIGN PATENT DOCUMENTS

JP    2007-088384 A    4/2007

OTHER PUBLICATIONS

Ibanescu et al., "Analysis of mode tructure in hollow dielectric waveguide fibers," 2003, Physical Review E, vol. 67, pp. 046608-1 to 046608-8.*

(Continued)

*Primary Examiner* — Kiho Kim
(74) *Attorney, Agent, or Firm* — Canon USA, Inc. IP Division

(57) ABSTRACT

Provided is a compact terahertz-wave generating apparatus that generates terahertz waves at high output and high efficiency. A terahertz-wave generating apparatus includes an electromagnetic-wave resonator including a hollow fiber in which an electromagnetic-wave gain medium is disposed, the electromagnetic-wave gain medium generating terahertz waves when exciting energy is supplied thereto, wherein the terahertz waves are amplified in the electromagnetic-wave resonator and are taken from the electromagnetic-wave resonator, wherein the diameter of the hollow fiber is set at one or more times and ten times or less as large as the inside diameter of the hollow fiber, in which the electromagnetic-wave gain medium is disposed, at which a cutoff frequency in a terahertz-wave propagation mode TE11 is provided.

18 Claims, 7 Drawing Sheets

(51) Int. Cl.
  *G01N 21/3581* (2014.01)
  *G01N 21/55* (2014.01)
  *G01N 21/59* (2006.01)
  *H01S 3/10* (2006.01)

(56) References Cited

U.S. PATENT DOCUMENTS

2007/0041417 A1  2/2007  Matsumoto et al.
2008/0296501 A1  12/2008  Breit et al.
2009/0097809 A1*  4/2009  Skorobogatiy et al. ....... 385/125

OTHER PUBLICATIONS

Xiao-Yong He, et al.; "Investigation on Propagation Properties of Terahertz Waveguide Hollow Plastic Fiber;" Optical Fiber Technolgy; 15, 2009; pp. 145-148.

Taiichi Otsuji; "First Success in Stimulated Emission of Terahertz Radiation From Graphene a New Material. First Big Step Ahead to a New Principle;" Tohoku University; Research Institute of Electrical Communication, Broadband Engineering Division, Ultra-Broadband Signal Processing; Jun. 19, 2009; pp. 1-7.

Igor Babushkin et al; "Generation of Terahertz Radiation From Ionizing Two-Color Laser Pulses in Ar Filled Metallic Hollow Waveguides;" Optics Express, Apr. 26, 2010, vol. 18, No. 9; pp. 9658-9663.

V. Ryzhii V et al: "Terahertz Lasers Based on Optically Pumped Multiple Graphene Structures With Slot-Line and Dielectric Waveguides;" Journal of Applied Physics 107 054505 (2010); pp. 1-5.

* cited by examiner

TERAHERTZ-WAVE GENERATING APPARATUS AND MEASURING UNIT EQUIPPED WITH THE SAME

TECHNICAL FIELD

The present invention relates to a terahertz-wave generating apparatus (THz wave emitter) and a measuring unit equipped with the same.

BACKGROUND ART

In recent years, a technique for measuring a sample to be measured in a nondestructive manner using electromagnetic waves in the frequency band from 0.03 THz or higher to 30 THz or lower (what is called terahertz electromagnetic waves, hereinafter also simply referred to as terahertz waves) has been developed. Specifically, the electromagnetic waves in this frequency band have been applied to, for example, an imaging technique for safe see-through examination that can substitute for fluoroscopy that affects human bodies, a technique that allows evaluation of the bonding state, the density, the mobility, etc. of a carrier in a substance by determining an absorption spectrum and a complex dielectric constant in the substance, and measurement of the membrane thickness of a sample.

Eric R Mueller et al. "2.5 $TH_Z$ Laser Local Oscillator for the EOS CHEM 1 Satellite", Proc. of the Ninth International Symposium on Space Terahertz Technology, p. 563 (1998) (hereinafter referred to as NPL 1) discloses a terahertz-wave generating apparatus in the form shown in FIG. 12.

The terahertz-wave generating apparatus shown in FIG. 12 irradiates a gas gain medium 1201, such as methanol, with exciting light 1204 using a $CO_2$ laser unit 1205 as a photo-exciting source to generate terahertz waves. The terahertz waves are amplified between a pair of mirrors 1202 and 1203 that constitute a resonator provided outside a gas cell 1207 in which the gain medium 1201 is sealed to output terahertz waves (laser waves) 1206 from the resonator due to induced emission. The gas cell 1207 is formed of a tube having a relatively large diameter, in which the electromagnetic waves seem to propagate freely.

On the other hand, Japanese Patent Laid-Open No. 2007-88384 (hereinafter referred to as PTL 1) discloses a laser beam source that emits a laser beam to a hollow fiber that contains rare gas to photoelectrically ionize the rare gas, thereby extracting ultraviolet light from an optical resonator.

The terahertz-wave generating apparatus disclosed in NPL 1 uses a cell with a length of 1.5 m as a cell that contains gas serving as a gain medium, and hence it is a large-sized apparatus whose occupation area is of the order of meter, thus being expensive. Furthermore, since the gas has a large capacity, and the mechanism for enclosing light is only a pair of mirrors placed in the laser oscillating direction, the power conversion efficiency for generating terahertz laser waves remains at about 0.7%, which is insufficient in reality.

Since the technique disclosed in PTL 1 is designed to irradiate the rare gas contained in the limited region in the hollow fiber with a laser beam to generate ultraviolet light, a compact apparatus configuration is possible as compared with a method of exciting gas in a free space. However, PTL 1 discloses an apparatus intended to generate ultraviolet light and has no intention to generate terahertz waves.

CITATION LIST

Patent Literature

PTL 1 Japanese Patent Laid-Open No. 2007-88384

Non Patent Literature

NPL 1 Eric R Mueller et al. "2.5 THZ LASER LOCAL OSCILLATOR FOR THE EOS CHEM 1 SATELLITE", Proc. of the Ninth International Symposium on Space Terahertz Technology, p. 563 (1998)

SUMMARY OF INVENTION

The present invention provides a compact terahertz-wave generating apparatus (THz wave emitter) that generates terahertz waves at high output and high efficiency.

A terahertz-wave generating apparatus according to an aspect of the present invention includes an electromagnetic-wave resonator including a hollow fiber in which an electromagnetic-wave gain medium is disposed, the electromagnetic-wave gain medium generating terahertz waves when exciting energy is supplied thereto, wherein the terahertz waves are amplified in the electromagnetic-wave resonator and are taken from the electromagnetic-wave resonator, wherein the diameter of the hollow fiber is set at one or more times and ten times or less as large as the inside diameter of the hollow fiber, in which the electromagnetic-wave gain medium is disposed, at which a cutoff frequency in a terahertz-wave propagation mode TE11 is provided.

The apparatus according to the aspect of the present invention is configured such that an electromagnetic-wave gain medium that generates terahertz waves in the hollow fiber, and the inside diameter of the hollow fiber is set at one or more times and ten times or less as large as an inside diameter at which a cutoff frequency in a terahertz-wave propagation mode TE11 is provided. The terahertz waves, which are generated since the electromagnetic-wave gain medium is disposed in the hollow fiber, propagate through the waveguide in the fiber and are trapped in the fiber, where they are used to excite terahertz waves by photon recycling, and hence terahertz waves can be efficiently generated. Furthermore, according to the aspect of the present invention, loss in the terahertz waves propagating in the hollow fiber can be reduced by setting the inside diameter of the hollow fiber is set within a specified range, thus allowing efficient generation of terahertz waves. This decreases threshold energy for oscillating terahertz waves and provides high-output oscillation.

DESCRIPTION OF EMBODIMENTS

The present invention is based on inventor's findings that loss in terahertz waves propagating in a hollow fiber can be reduced, and thus efficient generation of terahertz waves is possible by disposing an electromagnetic-wave gain medium that generates terahertz waves in the hollow fiber and setting the inside diameter of the hollow fiber to one time or more and ten times or less as large as an inside diameter at which a cutoff frequency in a propagation mode TE11 is obtained.

Embodiments of the present invention will be described hereinbelow with reference to the drawings.

Figure 1A:
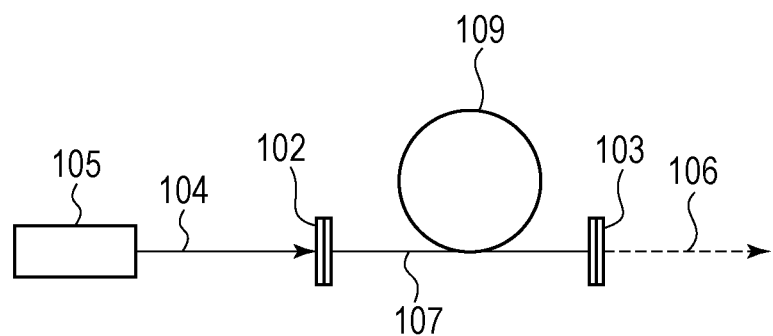
FIG. 1A is a schematic diagram illustrating a terahertz-wave generating apparatus according to an embodiment of the present invention.
Figure 1B:
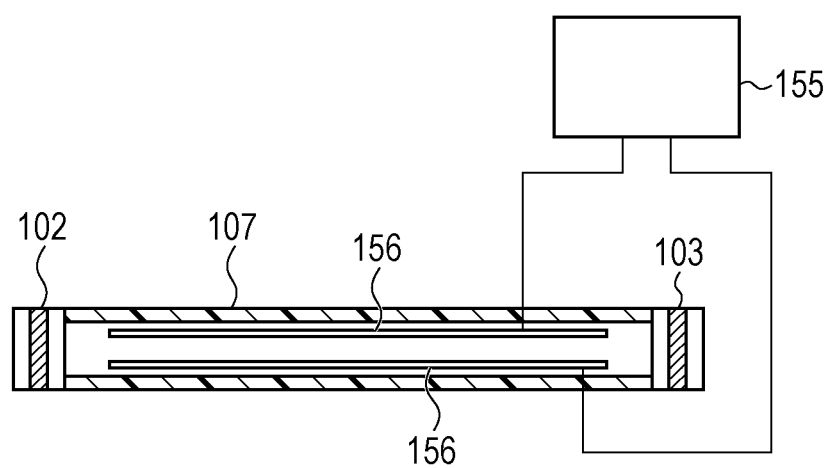
FIG. 1B is a schematic diagram illustrating a terahertz-wave generating apparatus according to an embodiment of the present invention.

FIGS. 1A and 1B are schematic diagrams illustrating a terahertz-wave generating apparatus according to an embodiment of the present invention. In FIG. 1A, the terahertz-wave generating apparatus includes an energy supply source 105 that supplies energy 104 for exciting a gain medium, a hollow fiber 107 in which an electromagnetic-wave gain medium is disposed which is supplied with the exciting energy 104 to generate terahertz waves, a wound portion 109 formed by winding the hollow fiber 107, and electromagnetic-wave resonators 102 and 103 that amplify the terahertz waves generated in the hollow fiber 107 while receiving the energy 104, and when amplification of the terahertz waves exceeding loss between the resonators 102 and 103 is given, laser oscillation occurs in the terahertz waves, and thus terahertz waves 106 are taken out. That is, the terahertz-wave generating apparatus of this embodiment emits the terahertz waves 106 in such a manner that the hollow fiber 107 in which a terahertz-wave gain medium is accommodated is disposed between the pair of resonators 102 and 103, to which the exciting energy 104 is supplied to oscillate the terahertz waves. Since the terahertz waves generated in the hollow fiber 107 are amplified, the present invention can also be interpreted as a terahertz-wave amplifier.

Here, the hollow fiber 107 is a generic term of fibers that use air as an electromagnetic-wave propagation layer, and any fibers that propagate terahertz waves that are electromagnetic waves can be adopted; a fiber with low propagation loss may be adopted.

Figure 2:
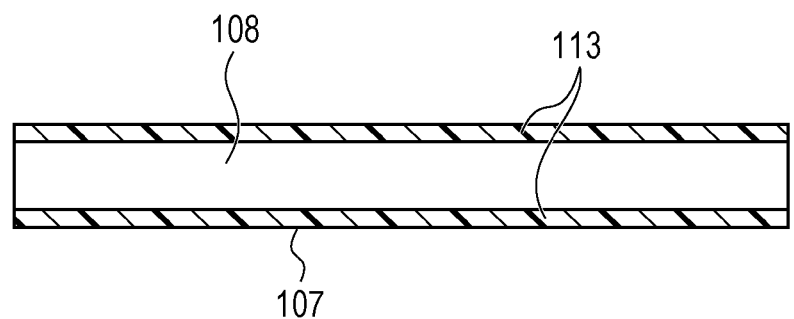
FIG. 2 is a schematic diagram of a resonator using a hollow fiber according to an embodiment of the present invention.
Figure 3:
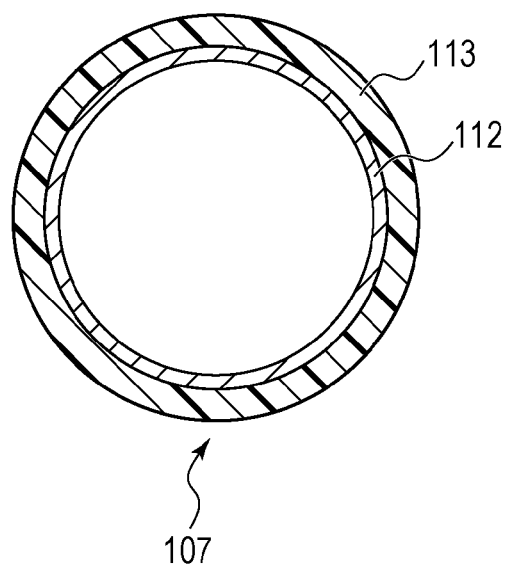
FIG. 3 is a cross-sectional view of the hollow fiber.

FIG. 2 is a cross-sectional view of the hollow fiber 107 taken in parallel to the terahertz-wave propagation direction. Reference sign 108 denotes a hollow portion, in which an electromagnetic-wave gain medium is disposed. A tube 113 that constitutes the hollow fiber 107 is formed of a polymeric plastic, such as polycarbonate. FIG. 3 is a cross-sectional view of the tube 113. As shown in FIG. 3, the hollow fiber 107 is formed by coating the inner surface with metal 112, such as silver and copper. That is, an example is a plastic fiber whose inner wall is coated with metal.

The inside diameter (size) of the hollow portion can be generally selected from the range of about 1 mm to 10 mm, and the length of the fiber can be selected from the range of about 10 cm to 10 m that satisfies the propagation mode conditions of the present invention. Although FIG. 1A shows an example in which part of the hollow fiber 107 is wound, a straight portion may be used depending on the length employed. The use of hollow fibers of these sizes to generate terahertz waves can also be a standard for application of the present invention.

In the terahertz-wave generating apparatus of the present invention, the inside diameter of the hollow fiber 107 is set at one time or more and ten times or less as large as the inside diameter of a hollow fiber in which an electromagnetic-wave gain medium is disposed and which exhibits a cutoff frequency in the terahertz-wave propagation mode TE11.

For propagation of electromagnetic waves in a guide tube (waveguide), there is a propagation natural mode of an electromagnetic field, derived from Maxwell's equations. The present invention adopts the way of thinking of the natural mode (propagation mode) for the hollow fiber 107.

The natural mode (propagation mode) in the waveguide has a cutoff frequency, in which only frequencies higher than or equal to the cutoff frequency can be propagated, and electromagnetic waves with frequencies less than that are not propagated.

Electromagnetic waves whose electric field in the direction in which the electromagnetic waves propagates in the waveguide is zero are referred to as TE waves (transverse electric waves), and electromagnetic waves whose magnetic field in the propagating direction is zero are referred to as TM waves (transverse magnetic waves). Electromagnetic waves in these modes propagate also in the hollow fiber 107 employed in the present invention.

The hollow fiber is regarded as a circular waveguide, and the relationship between losses and frequencies in the TE11 mode, which is a lower-order basic mode of the circular waveguide, was calculated.

Figure 4:
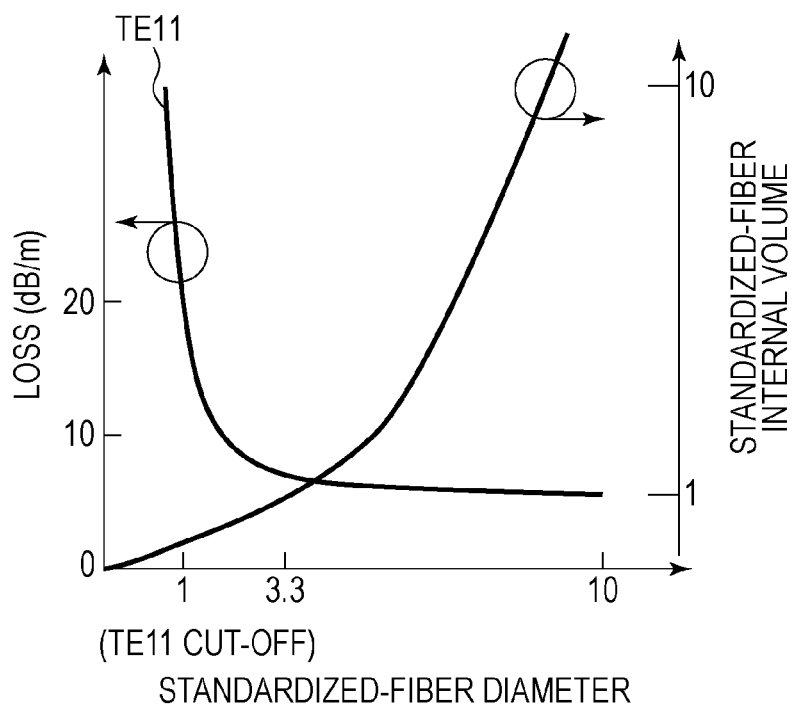
FIG. 4 is a graph showing the relationship among fiber diameters, losses, and fiber internal volumes of hollow fibers in a propagation mode TE11.

FIG. 4 shows a graph in which the calculation results were plotted with inside diameters of fibers whose frequencies are standardized (on the basis of the relationship between the diameter (2a) of the hollow fiber 107 and a wavelength λ) as a horizontal axis against losses as a vertical axis. The vertical axis at the left in FIG. 4 indicates losses, and the vertical axis at the right indicates the internal volumes of fibers having a length of 1m. The fiber internal volumes indicated on the vertical axis are values standardized on the basis of 1 in the case where the fiber diameter is 3.3.

In FIG. 4, in the case where the fiber inside diameter is 10, the fiber internal volume is approximately 100 times as large as that in the case where the fiber inside diameter corresponding to the cutoff frequency is 1. Thus, threshold electricity generated due to oscillation of the terahertz waves is also approximately 100 times. Since electricity applied for laser oscillation is limited, the present invention sets the inside diameter in the range of one time or more and ten times or less as large as the inside diameter of the standardized fiber (one time or more and ten times or less as large as an inside diameter at which a cutoff frequency in the TE11 mode is exhibited). The inside diameter may be set in the range from one time or more to five times or less as large as an inside diameter at which a cutoff frequency in the TE11 mode is exhibited.

Figure 5:
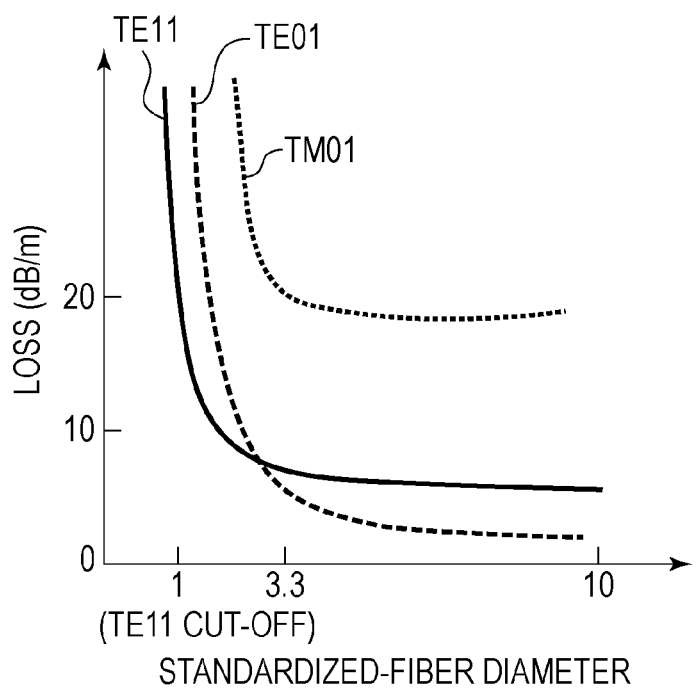
FIG. 5 is a graph in which losses in the propagation mode TE11, a propagation mode TE01, and a propagation mode TM01 caused in hollow fibers are plotted.

FIG. 5 is a graph in which losses in a TE01 mode and a TM01 mode, in addition to the TE11 mode, caused in fibers are plotted. At fiber diameters corresponding to the cutoff frequency in the TE01 mode, losses in the TE01 mode are larger than those in the TE11 mode. However, as the fiber diameter increases, the losses in the TE01 mode decrease more. The graph in FIG. 5 shows calculations on straight hollow fibers. In the case of wound hollow fibers, the degree of loss differs from that in this graph.

Propagation modes that are generally expressed as TEmn and TMmn are natural modes derived from wave equations of TE waves and TM waves derived from Maxwell's equations. They can be determined by solving a partial differential equation under a boundary condition. The numerical subscripts of TEmn are simply expressed as follows: for a circular fiber, m is the order in the circumferential direction, and n is the number of tubes at which the electric field is 0. For the numerical subscripts of TMmn, similarly, m is the order in the circumferential direction, and n is the number of tubes at which the magnetic field is 0.

In the present invention, terahertz waves are electromagnetic waves in the frequency band from 0.03 THz or more to 30 THz or less (from 1 mm to 10 μm in terms of wavelength).

In the present invention, examples of the exciting energy to be supplied to an electromagnetic-wave gain medium that generates terahertz waves includes a laser beam serving as electromagnetic-wave energy, such as $CO_2$ laser, high-frequency energy serving as electric energy, such as RF, and electron-beam energy.

FIG. 1B shows a terahertz-wave generating apparatus configured using electric energy from an RF power source as exciting energy. In the apparatus shown in FIG. 1B, an RF power source 155 is connected to an electrode 156 placed in the hollow fiber 107, and RF energy is supplied into the hollow fiber 107.

An electromagnetic-wave gain medium that generates terahertz waves can be selected from gas, solid, and liquid. Examples of the gas include methanol, ethanol, and water vapor. Examples of the solid include graphene. Examples of the liquid include alcohol and water.

The terahertz-wave generating apparatus of the present invention may also be configured as an apparatus that is equipped with a modulator that modulates the intensity of terahertz waves in the electromagnetic-wave resonator and that sweeps the wavelength of terahertz waves extracted from the electromagnetic-wave resonator by changing the frequency applied to the modulator.

The present invention further includes a measuring unit including the terahertz-wave generating apparatus of the present invention; a detector that detects terahertz waves reflected by or passing through an analyte to be measured, the terahertz waves being obtained by irradiating the analyte with terahertz waves generated from the terahertz-wave generating apparatus; and a display unit that displays information on the analyte on the basis of a detection signal detected by the detector.

The present invention will be described in detail below using specific examples.

EXAMPLES 1 TO 4 AND COMPARATIVE EXAMPLE 1

An example in which a $CO_2$ laser (carbon dioxide laser) is used as an exciting energy source will be described with reference to FIGS. 1A and 1B and so on.

FIGS. 1A and 1B are schematic diagrams of the terahertz-wave generating apparatus of this example.

The exciting light (energy) 104 emitted from the exciting $CO_2$ laser source (energy supply source) 105 passes through the terahertz-band reflecting mirror (resonator) 102 and is incident on the hollow fiber 107. The incident exciting light 104 is absorbed by a gas medium composed of methanol disposed in the hollow fiber 107 to excite the gas medium and causes terahertz light to be generated from the gas medium due to energy transition based on the rotational level of the gas molecules.

The generated terahertz light is trapped between the resonators 102 and 103 that hold the hollow fiber 107, and when amplification of the terahertz waves exceeding loss in the resonators 102 and 103 occurs, laser oscillation occurs to generate the terahertz waves 106.

The hollow fiber 107 is designed to have a minimum volume of a gas medium and to achieve the propagation mode TE11 in which the optical loss is small. The fact that the propagation mode is TE11 is confirmed by measuring the electric field distribution of the terahertz waves emitted from a window reflecting mirror that constitutes the resonator 103 using a beam profiler.

The hollow fiber 107 is constituted of a polycarbonate tube with a thickness of 200 μm and a length of 1 m having a silver-coat of 2 μm on the inner wall thereof, in which the inside diameter of the hollow portion is about 3 mm (corresponding to the standardized fiber diameter 3.3 shown in FIG. 4).

A specific assembly method of the apparatus will be described hereinbelow.

Figure 6:
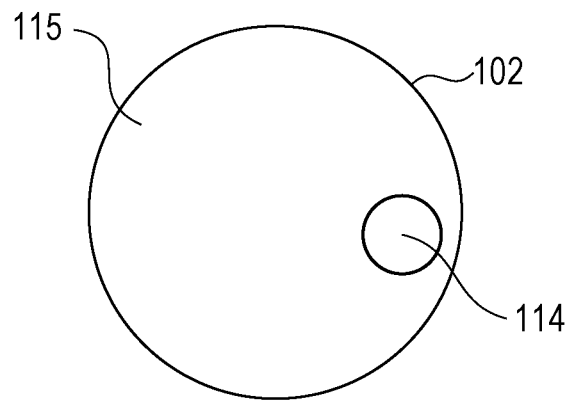
FIG. 6 is a schematic diagram of a reflecting mirror (window reflecting mirror).

The terahertz-band reflecting mirror 102 is configured such that a gold thin film 115 with a thickness of 0.2 μm is deposited on the surface of a polymethylpentene with a thickness of 1 mm, and a window 114 for receiving the exciting light 104 is provided therein, as shown in FIG. 6. The diameter of the window 114 is set at about 0.7 mm.

The window 114 is located at about 0.1 μm from the periphery, and the reflectance is set at about 80%. The terahertz-band reflecting mirror 102 is secured to an end face of the hollow fiber 107 using plastic so that there is no gap through which the sealed gas passes.

The window reflecting mirror 103 through which terahertz light is taken out is a mirror in which about ten pairs of polypropylene and polymethylpentene are alternately deposited in a thickness of 52.5 μm/51.4 μm on the surface of polymethylpentene having a thickness of 1 mm to allow light with 1 THz to 10 THz to pass therethrough. With this configuration, the reflectance is 75%, and the transmittance is about 20% in the band from 1 to 10 THz. After a methanol gas is sealed in the hollow fiber 107, the window reflecting mirror 103 and the hollow fiber 107 are secured with plastic without gap.

The length between the resonators 102 and 103 is set at 1 m, and a methanol gas with a laser reflectance of 60% and a purity of about 99% is sealed in the hollow fiber 107 under a reduced pressure (695 mTorr) to constitute the terahertz-wave generating apparatus.

The apparatus of this example provides an oscillating wavelength of 96.5 μm, a threshold optical power of 100 mW, and a slope efficiency of 2%. If the power of the exciting light 104 is 1 W, the terahertz output is about 18 mW. The power conversion efficiency here is 1.8%.

In Example 2, a terahertz-wave generating apparatus is configured similarly to Example 1 except that the inside diameter of the hollow fiber 107 is set at 2 mm (corresponding to a standardized fiber diameter 2.2 shown in FIG. 4).

With the apparatus of this example, since the inside diameter of the hollow fiber 107 is decreased, the excitation gas volume is about half of that in Example 1, and thus the threshold optical power can be reduced, but the propagation loss increases to 10 dB/m, and thus an eventual threshold optical power output increases to about 320 mW. The slope efficiency is about 1%, and thus, if the power of the exciting light 104 is 1 W, the terahertz output is 7 mW, and the power conversion efficiency is 0.7%.

In Example 3, a terahertz-wave generating apparatus is configured similarly to Example 1 except that the inside diameter of the hollow fiber 107 is set at 4.5 mm (corresponding to a standardized fiber diameter 5 shown in FIG. 4).

The threshold optical power is about 300 mW, and if the power of the exciting light 104 is increased to 1 W or more, the slope efficiency is about 1.8%, which is similar to that of Example 1. If the power of the exciting light 104 is set at 1 W, the terahertz output is 4 mW, and the power conversion efficiency is 1.4%.

In Example 4, a terahertz-wave generating apparatus is configured similarly to Example 1 except that the inside diameter of the hollow fiber 107 is set at 9 mm (corresponding to a standardized fiber diameter 10 shown in FIG. 4).

With the apparatus of this example, the excitation gas volume increases to about ten times that of Example 1, and the propagation loss is about 7 dB/m, which is substantially equal to that of Example 1. As a result, the threshold optical power is about 1000 mW, which is decreased from that of Example 1. If the power of the exciting light 104 is increased to 1 W or more, the slope efficiency is about 1.8%, which is similar to that of Example 1. If the power of the exciting light 104 is 2 W, the terahertz output is 7 mW.

As Comparative Example 1, a terahertz-wave generating apparatus is configured similarly to Example 1 except that a hollow fiber having an inside diameter of 10 mm (corresponding to a standardized fiber diameter 11 shown in FIG. 4) is employed.

In Comparative Example 1, the excitation gas volume is ten or more times as large as that of Example 1, and if the propagation loss is substantially at the same level, terahertz waves are not oscillated if the upper limit of the exciting light 104 is at 1 W.

Example 5

An apparatus in which a solid gain medium is used as a gain medium in the hollow fiber 107 will be described.

Figure 7:
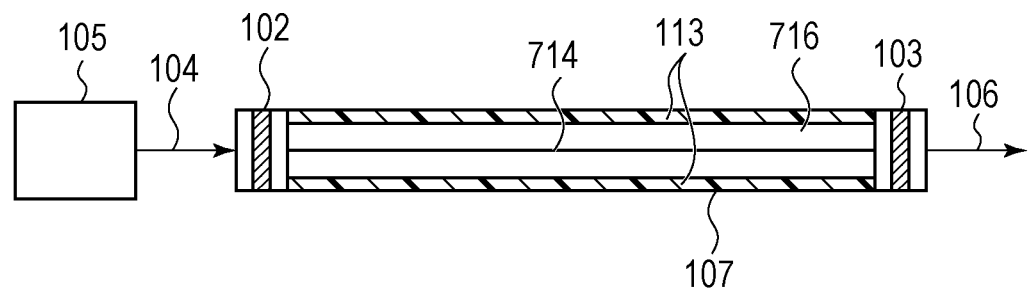
FIG. 7 is a diagram illustrating an example of a terahertz-wave generating apparatus in which a solid gain medium is disposed in a hollow fiber.

FIG. 7 shows a schematic diagram of the apparatus of this example. In the apparatus shown in FIG. 7, the exciting light 104 is introduced into the hollow fiber 107 by the exciting laser source 105, such as a $CO_2$ laser source, via the terahertz-band reflecting mirror 102.

The introduced exciting light 104 is absorbed by a solid excitation medium 714, such as a graphene thin film and a graphene inner wall layer, and a methanol gas 716 into an excited state to generate terahertz light due to energy transition in the band.

The generated terahertz light is trapped between the resonators 102 and 103 that hold the hollow fiber 107, where amplification of the terahertz light exceeding an optical loss in the resonators 102 and 103 occurs to cause laser oscillation. The oscillation frequency is about 1 THz to 6 THz, which depends on the length between the resonators 102 and 103.

Figure 8A:
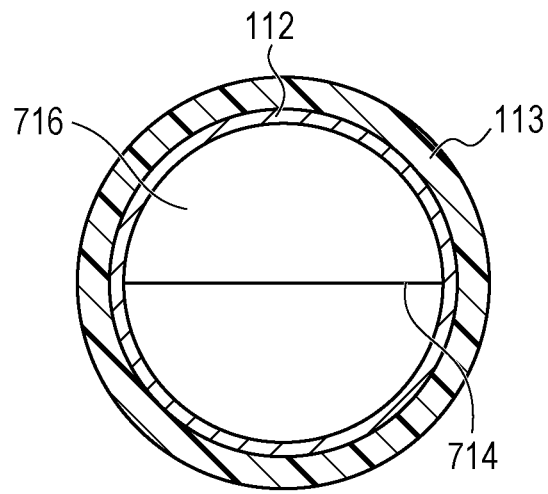
FIG. 8A is a cross-sectional view of a hollow fiber in which a solid gain medium is disposed therein.
Figure 8B:
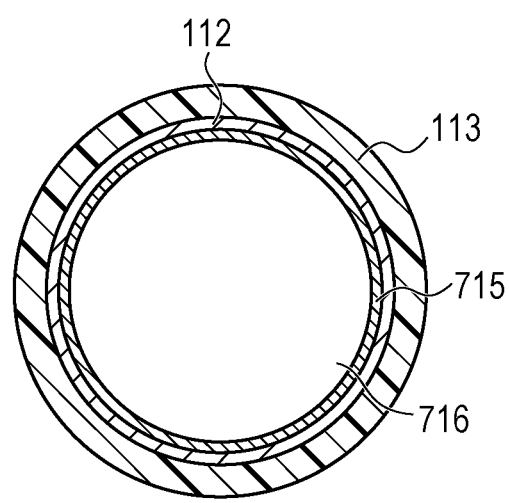
FIG. 8B is a cross-sectional view of a hollow fiber in which a solid gain medium is disposed therein.

Example 5 will be described in detail with reference to FIGS. 8A and 8B. The arrangements of the graphene gain thin film (solid excitation medium) 714 and a graphene inner wall layer 715 are shown in FIGS. 8A and 8B, respectively. The silver coat 112 with a thickness of about 2 μm is formed by vapor plating in the polycarbonate tube 113 with a thickness of about 200 μm that forms the hollow fiber 107, and the methanol gas 716 and the graphene gain thin film 714 are arranged and fixed as shown in FIG. 8A.

The length of the graphene gain thin film 714 is set at 10 mm to 100 mm. The methanol gas 716 fills the interior of the hollow fiber 107 under a reduced pressure of 120 mTorr. The length between the resonators 102 and 103 is 10 mm to 100 mm, which is about 1/10 to 1/100 of a case where gas is used as an excitation medium.

FIG. 8B shows an arrangement in which the graphene inner wall layer 715 is deposited on the silver coat 112. One or two graphene layers 715 are deposited inside the hollow fiber 107, and the interior is filled with the methanol gas 716.

Terahertz waves are generated, with the other conditions set to be the same as those of Example 1.

Example 6

Figure 9:
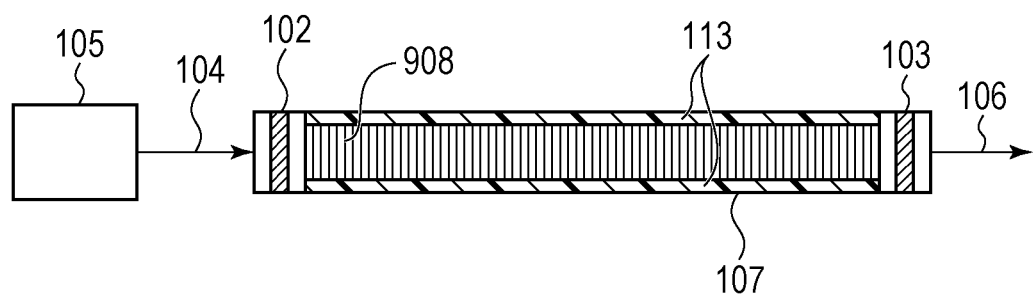
FIG. 9 is a diagram illustrating an example of a terahertz-wave generating apparatus in which a liquid gain medium is disposed in a hollow fiber.

Referring to FIG. 9, an apparatus in which a liquid gain medium is disposed in the hollow fiber 107 will be described. The apparatus of this example is characterized in that liquid 908 serving as an excitation medium is disposed in the hollow fiber 107. Examples of the liquid include alcohol and water.

Example 7

A terahertz-wave laser unit whose oscillation wavelength is variable will be described. The apparatus of this example can change the wavelength at high speed.

Figure 10:
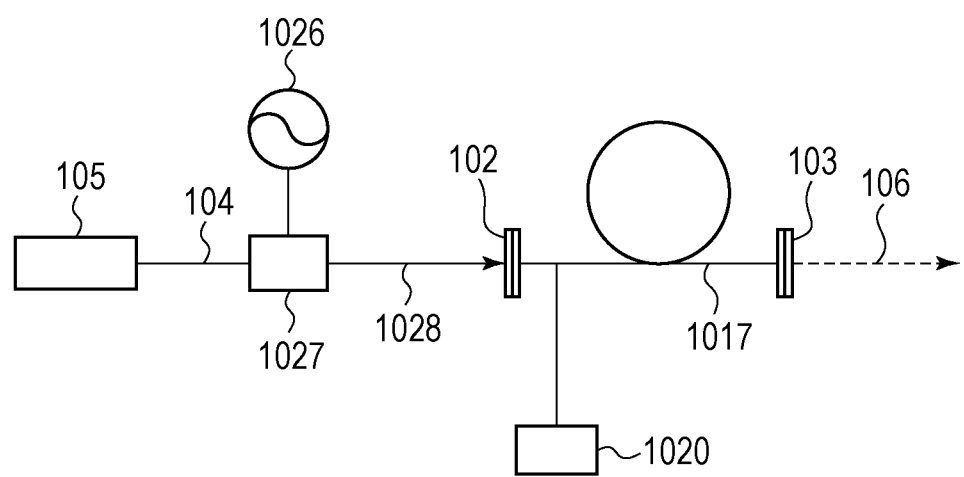
FIG. 10 is a schematic diagram illustrating an example of a wavelength-variable terahertz-wave generating apparatus.

FIG. 10 shows the apparatus of this example configured as a forced mode-locking laser unit.

The apparatus of this example employs a hollow fiber 1017 whose refractive index exhibits strong dispersion relative to wavelength (refractive index dispersion) as a waveguide of the resonators 102 and 103 and adopts a dispersion tuning that allows variable wavelength by sweeping the frequency applied to an optical modulator 1027.

The exciting light 104 output from the exciting laser source 105, such as a $CO_2$ laser, is introduced into the optical modulator 1027, such as an electro-optical modulator (EOM). The optical modulator 1027 receives a sinusoidal intensity-modulation signal having a repetition frequency of about 300 MHz from an RF signal source 1026.

The modulation signal is adjusted to about an integer multiple of a free spectrum range depending on the length between the resonators 102 and 103 and causes mode-locked oscillation between the resonators 102 and 103.

An intensity-modulating optical signal 1028 passes through the terahertz-band reflecting mirror 102 and enters the hollow fiber 1017.

The incident intensity-modulating optical signal 1028 is absorbed by a gas medium in the hollow fiber 1017, where it is excited to generate terahertz waves due to energy transition based on the rotational level of the gas molecules.

The generated terahertz waves are trapped between the resonators 102 and 103 that hold the hollow fiber 1017, and when amplification of the terahertz waves exceeding a loss in the resonators 102 and 103 occurs, laser oscillation occurs.

The hollow fiber resonator is designed to have the terahertz light propagation mode TE01.

The outermost layer of the hollow fiber 1017 is a polycarbonate tube 513 with a thickness of about 200 μm, whose inner surface is coated with silver with a thickness of about 2 μm, on the inner surface of which a polymer layer with a thickness of about 25 µm is formed. The inside diameter of the hollow portion is about 3 mm.

Laser characteristics in the case where the length between the resonators 102 and 103 is 1 m, in which a methanol gas with a laser reflectance of 60% and a purity of about 99% is disposed under a pressure of 695 mTorr reduced by a gas-pressure regulator 1020, are as follows: the oscillation wavelength is 96 µm, the threshold optical power is 100 mW, and the slope efficiency is 0.005%. If the power of the intensity modulating optical signal 1028 is at 200 mW, the pulse output of the terahertz waves 106 is about 0.5 mW, and the repetition frequency is 300 MHz.

With the apparatus of this example, the oscillation waveform can be changed by changing a frequency applied from the RF signal source 1026. Expected group velocity dispersion in the hollow fiber 1017 is 0.1 to 15 ps/TH cm. If sufficient dispersion can be obtained in a dispersion tuning operation with the length of the electromagnetic-wave resonator set at 1 m or more, the wavelength can be swept in the range from 96.0 µm to 96.48 µm, which is the laser oscillation wavelength of the methanol gas. In this case, the oscillation frequency is from 300 MHz to 302.297 MHz, and in the case where the power of the intensity modulating optical signal 1028 is at 200 mW, the output is about 2 mW.

Example 8

An example in which the terahertz-wave generating apparatus of the present invention is applied to a measuring unit will be described.

Figure 11:
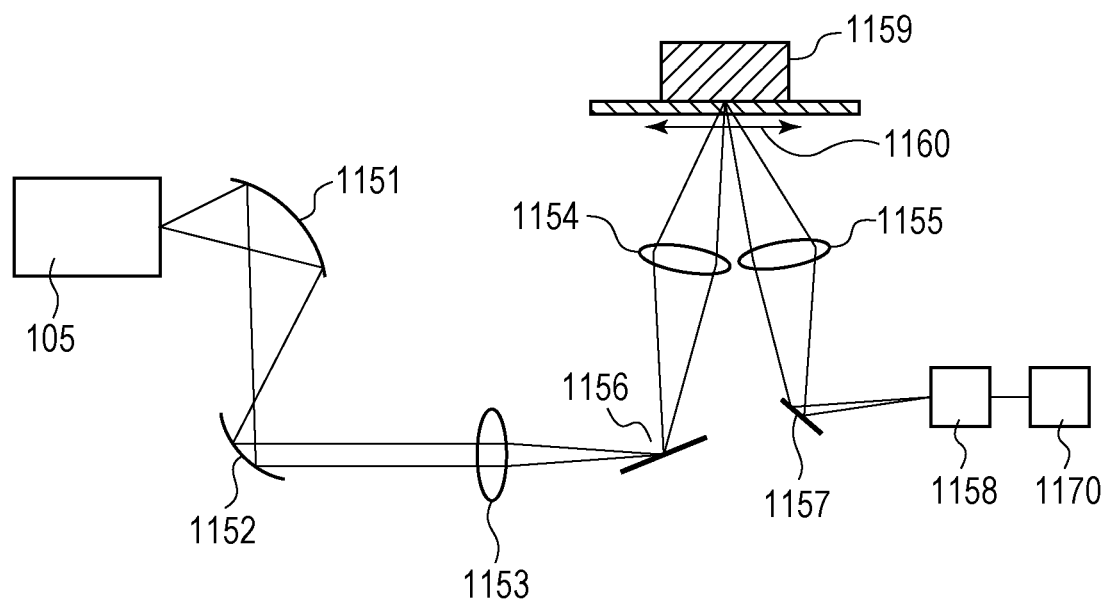
FIG. 11 is a schematic diagram illustrating an example of a measuring unit in which a terahertz-wave generating apparatus according to an embodiment of the present invention is used as a terahertz wave generator.
Figure 12:
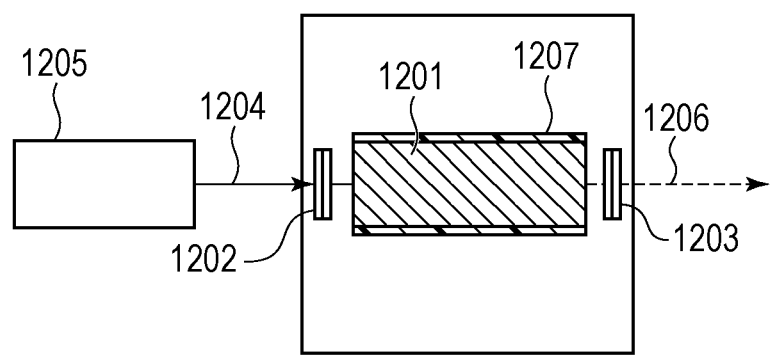
FIG. 12 is a schematic diagram illustrating a known terahertz-wave generating apparatus.

FIG. 11 shows a measuring unit for obtaining the internal information of an analyte, in which the terahertz-wave generating apparatus of the present invention is applied to a terahertz-wave generation source.

In FIG. 11, reference sign 105 denotes a THz-wave generator that uses the terahertz-wave generating apparatus of the present invention. Here, the generator 105 has an oscillation frequency of about 3 THz and an output of 30 mW.

The THz waves generated from the THz-wave generator 105 is collimated into collimated beams with a beam diameter of about 12 mm using parabolic mirrors 1151 and 1152, and the collimated beams are collected and radiated onto the bottom of an analyte 1159 using lenses 1153 and 1154. Here, the analyte 1159 can be an article, such as a baggage and a bag, a body part, such as a hand and a leg, and so on.

At that time, a dual-axis galvanometer mirror 1156, which is a two-dimensional polarizer, is operated to scan the bottom of the analyte 1159 in two dimensions as indicated by arrow 1160.

The THz waves reflected by the bottom of the article are detected by a THz-wave detector 1158 via a lens 1155 and a reflecting mirror 1157. The detector 1158 combines two-dimensional tomographic images of the individual level planes of the analyte 1159 in the depthwise direction on the basis of the detection signal, and the tomographic image obtained as analyte information is displayed on a display (liquid-crystal display unit or the like) 1170. In this example, a pyroelectric detector using deuterated L-alanine-doped triglycene sulphate (DLATGS) crystal or the like is used as the detector.

In this example, after one item of scan image information is obtained, the output power of the THz waves is gradually increased one step by one step (one unit by one unit). Here, the output power is increased at intervals of 100 µl at every cycle in which one item of scan image information is obtained, and the examination of the analyte is finished.

Since the beam scanning method uses THz wave power through collection of light, permeability to an article increases (that is, the depth of permeability to an article increases as the output power increases), and the SN ratio of the acquired image increases. Scan images of the individual level planes are acquired, for example, by acquiring arithmetically processed information of detection signals obtained at different output powers one-step-by-one-step at the individual scanned portions and plotting them in correspondence with the scanning positions. Since the terahertz-wave generating apparatus of the present invention can provide a relatively high output, a good SN ratio can be achieved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-106229, filed May 11, 2011, which is hereby incorporated by reference herein in its entirety.

REFERENCE SIGNS LIST

102, 103 electromagnetic-wave resonator
104 exciting energy
106 terahertz waves
107 hollow fiber.

The invention claimed is:

1. A terahertz-wave generating apparatus comprising:
an electromagnetic-wave resonator including a hollow fiber in which an electromagnetic-wave gain medium is disposed, the electromagnetic-wave gain medium generating terahertz waves when exciting energy is supplied thereto, wherein the terahertz waves are amplified in the electromagnetic-wave resonator and are taken from the electromagnetic-wave resonator,
wherein the diameter of the hollow fiber is set at one or more times and ten times or less as large as the inside diameter of the hollow fiber, in which the electromagnetic-wave gain medium is disposed, at which a cutoff frequency in a terahertz-wave propagation mode TE11 is provided.

2. The terahertz-wave generating apparatus according to claim 1, wherein terahertz waves in one of propagation modes TE11, TE01, and TM01 are generated in the hollow fiber having said inside diameter.

3. The terahertz-wave generating apparatus according to claim 1, wherein the hollow fiber is a plastic fiber whose inner wall is coated with metal.

4. The terahertz-wave generating apparatus according to claim 3, wherein the metal is silver.

5. The terahertz-wave generating apparatus according to claim 1, wherein the exciting energy is an electromagnetic wave.

6. The terahertz-wave generating apparatus according to claim 5, wherein the electromagnetic wave is emitted from a laser unit.

7. The terahertz-wave generating apparatus according to claim 6, wherein the laser unit is a carbon dioxide laser.

8. The terahertz-wave generating apparatus according to claim 1, wherein the exciting energy is electric energy.

9. The terahertz-wave generating apparatus according to claim 8, wherein the electric energy is high-frequency energy.

10. The terahertz-wave generating apparatus according to claim 1, wherein the exciting energy is electron-beam energy.

11. The terahertz-wave generating apparatus according to claim 1, wherein the electromagnetic-wave gain medium is gas.

12. The terahertz-wave generating apparatus according to claim 11, wherein the gas is one of methanol, ethanol, and water vapor.

13. The terahertz-wave generating apparatus according to claim 1, wherein the electromagnetic-wave gain medium is solid.

14. The terahertz-wave generating apparatus according to claim 13, wherein the solid is graphene.

15. The terahertz-wave generating apparatus according to claim 1, wherein the electromagnetic-wave gain medium is liquid.

16. The terahertz-wave generating apparatus according to claim 15, wherein the liquid is either alcohol or water.

17. The terahertz-wave generating apparatus according to claim 1, further comprising a modulator that modulates the intensity of the terahertz waves in the electromagnetic-wave resonator, wherein the wavelength of terahertz waves taken from the electromagnetic-wave resonator is swept by changing a frequency applied to the modulator.

18. A measuring unit comprising:
the terahertz-wave generating apparatus according to claim 1;
a detector that detects terahertz waves reflected by or passing through an analyte to be measured, the terahertz waves being obtained by irradiating the analyte with terahertz waves generated from the terahertz-wave generating apparatus; and
a display unit that displays information on the analyte on the basis of a detection signal detected by the detector.

* * * * *